United States Patent [19]

Mitsuhashi

[11] Patent Number: 4,745,053

[45] Date of Patent: May 17, 1988

[54] PROCESS FOR PRODUCING HUMAN INTERFERON AND METHOD FOR ASSAYING THE INTERFERON PRODUCTIVITY OF BLOOD

[75] Inventor: Masakazu Mitsuhashi, Okayama, Japan

[73] Assignee: Kabushiki Kaisha Hayashibara Seibutsu Kagaku Kenkyojo, Okayama, Japan

[21] Appl. No.: 624,752

[22] Filed: Jun. 26, 1984

[30] Foreign Application Priority Data

Jul. 8, 1983 [JP] Japan .................................. 58-125152
Jul. 8, 1983 [JP] Japan .................................. 58-125153

[51] Int. Cl.$^4$ .................................. C12Q 1/70; C12Q 1/02; G01N 33/53
[52] U.S. Cl. .................................. 435/5; 435/29; 435/7; 435/811; 436/63; 436/64; 436/813
[58] Field of Search .................................. 435/811, 4, 68, 7, 5, 435/29; 424/85; 260/112 R; 436/63, 64, 86, 813

[56] References Cited

U.S. PATENT DOCUMENTS 4,296,025 10/1981 Sugimoto .................................. 260/112 R
4,490,357 12/1984 Skurkovich et al. .................................. 424/85
4,514,507 4/1985 Secher .................................. 436/518

FOREIGN PATENT DOCUMENTS 49-06111 1/1974 Japan .
53-94008 8/1978 Japan .

OTHER PUBLICATIONS

Salk, "J. of Immunol.", vol. 49 (1944), pp. 87-98.
Pidot, "Applied Microbiol.", vol. 22, No. 4 (1971), pp. 671-677.
Strander et al, "Ann. Med. Exp. Fenn.", 44 (1966), pp. 265-273.
Flow Laboratories, Inc., "Product Catalog", FM 740, (1983), pp. 44-45 & 70.
Horn et al, Chem. Abstracts, 98:32791y, p. 515 (1983), "Interferon as Possible Tumor Marker in Breast Cancer", Proc. Trienn. World Cong. World Assoc. Soc. Pathol. (Anat. Clin.), 1981 (pub. 1982), 1, 277-282.

Primary Examiner—Esther M. Kepplinger
Attorney, Agent, or Firm—Browdy & Neimark

[57] ABSTRACT

A process for producing HuIFN using whole human blood and a method for assaying the blood interferon (HuIFN) productivity are disclosed. The whole blood is incubated in the presence of an anticoagulant (e.g. heparin, ACD, and CPD) and a viral inducer under the conditions appropriate to accumulate a substantial amount of HuIFN. The blood HuIFN productivity determined by titrating the accumulated HuIFN with a suitable procedure (bioassay, radioimmunoassay, or enzyme-linked immunosorbent assay) is useful in clinical test to detect cancer in its early stage. The HuIFN per se is recovered, and purified prior to its prophylactic and therapeutic uses.

20 Claims, No Drawings

PROCESS FOR PRODUCING HUMAN INTERFERON AND METHOD FOR ASSAYING THE INTERFERON PRODUCTIVITY OF BLOOD

FIELD OF THE INVENTION

The present invention relates to a process for producing human-specific interferon (abbreviated as "HuIFN" hereinafter) using whole human blood and to a method for assaying the HuIFN productivity of human blood.

DESCRIPTION OF THE PRIOR ART

In recent years, clinical tests whereby the level of a blood enzyme or its metabolite is determined chemically have been in a wide use.

Since HuIFN, a blood component, exhibits antiviral- and antitumor activities, it has been proposed to include the level of serum HuIFN in the items of clinical test. Such proposal, however, has not been realized because serum HuIFN is minute.

Blood consists of a fluid, plasma, in which are suspended formed elements such as erythrocyte, leukocyte and platelet. One $mm^3$ blood generally contains, in addition to $7.4 \times 10^3$ leukocytes and $3 \times 10^5$ platelets in adult, $5.4 \times 10^6$ erythrocytes in man or $4.8 \times 10^6$ in woman.

It is well known that HuIFN is produced by human leukocytes.

In conventional processes to produce HuIFN, viable leukocytes separated from human blood are used. For example, as is evident from Hans Strander and Kari Cantell, *Ann. Med. Exp. Fenn.*, Vol. 44, pp. 265–273 (1966), and the specifications of Japan Patent Kokai Nos. 6,111/74 and 94,008/78, leukocytes are separated from other elements present in whole blood, and then allowed to produce HuIFN.

Detailed studies on these conventional processes confirmed that they, however, give a low recovery yield of leukocytes from blood, i.e. 30–50%, and damage leukocytes during the separation to lower the viability to 40–60% and, eventually, the overall recovery yield to 10–30%, as well as that the separated leukocytes give an inconsistent HuIFN production, these facts render the estimation of the HuIFN productivity of blood very difficult, and cause an obstacle in mass-production of HuIFN.

DETAILED DESCRIPTION OF THE INVENTION

As the result of his research into the mass-production of HuIFN using precious human blood, as well as for the assay of the HuIFN productivity by use of donated blood, the present inventor eventually found that a large amount of HuIFN can be readily produced with an ease by incubating a whole blood sample in a vessel while exposing the whole blood to an anticoagulant and a virus. The present inventor also found that the HuIFN productivity of whole blood can be readily determined with high reproducibility by incubating whole blood in a vessel while exposing the whole blood to an anticoagulant and a virus, and titrating the accumulated HuIFN.

Detailed studies have confirmed that the exposure to an intact or inactivated virus of an amount of 20–200,000 HA/ml whole blood is favorable. "HA" represents the unit of the haemagglutination titer of a virus.

The wording of "whole blood" means fresh blood preparations collected from donors, and also suspensions which are obtained by removing plasma liquid from such blood preparations and suspending the residual formed elements in an suitable non-plasma liquid, e.g. physiological saline, buffer solution or nutrient culture medium.

Any anticoagulant capable of preventing the coagulation of such whole blood and does not affect HuIFN production is usable in the invention. For example, heparin, acid citrate-dextrose (ACD) and citrate-phosphate-dextrose (CPD) are favorable.

The viruses usable in the invention are those which are capable of inducing HuIFN production in the whole blood. For example, Sendai virus or Newcastle disease virus may be used intact or after inactivation. The inactivated viruses usable in the invention include those whose reproductivities are partially or completely suppressed, for example, by uv-irradiation, heating or treatment at an extreme pH. An appropriate range for inoculum of the virus is 20–20,000 HA/ml whole blood.

The step of incubating the whole blood in a vessel while exposing the whole blood to the anticoagulant and virus is carried out in such a manner that the whole blood is exposed in the vessel to the anticoagulant and virus to produce HuIFN. For example, to the prescribed amounts of the anticoagulant and virus in the vessel is added an appropriate amount of the whole blood, and the mixture is incubated therein. Alternatively, a mixture of the anticoagulant and whole blood is placed in a vessel, added with the virus, and incubated. In this incubation step, a suitable medium, e.g. physiological saline, isotonic buffer solution or nutrient culture medium, may be used additionally.

Tank, jar, flask, test tube, ampule and micro plate well of any shape and volume may be used as the vessel in the invention.

The incubation conditions are those under which HuIFN is producible: for example, temperature range of 30°–40° C.; and incubation time, 5–50 hours. In this case, priming or superinduction may be carried out if necessary.

After incubation to produce HuIFN and an optional dilution with physiological saline or isotonic buffer solution, the whole blood is then separated with suitable procedure(s), such as centrifugation or filtration, to remove formed elements such as blood cells, and the resultant supernatant or filtrate containing HuIFN is subjected to purification or titration.

The HuIFN can be purified to obtain an HuIFN preparation having the highest possible purity by combination of conventional procedures, e.g. salting-out, dialysis, filtration, concentration, adsorption and desorption by ion exchange, gel filtration, affinity chromatography using a suitable ligand such as antibody, isoelectric point fractionation and electrophoresis.

The obtained HuIFN is advantageously feasible as injection or drug for external or internal use in the prevention and treatment of human diseases, alone or in combination with one or more other substances.

The HuIFN productivity of human whole blood can be determined according to the invention by titrating the HuIFN level in the above described supernatant or filtrate. For the purpose of such titration, any assay can be used as long as the HuIFN production by the whole blood is titrated therewith; e.g. bioassay, radioimmunoassay and enzyme-linked immunosorbent assay.

In recent years, enzyme-linked immunosorbent assay has been developed as a highly safe, convenient and speedy assay. Any enzyme-linked immunosorbent assay capable of titrating IFN as the antigen is employable in the invention. For example, double antibody sandwich technique and modified double antibody sandwich technique are favorable.

It was confirmed that the HuIFN productivities determined in this way are very useful for clinically testing the individual donor.

The method according to the invention confirmed that the blood collected from a cancer patient is much lower in blood HuIFN productivity than those collected from healthy volunteers.

The following experiments further explain the present invention.

EXPERIMENT 1

Effect of Pretreatment on the HuIFN Productivity of Blood

The effect of pretreating blood on the productivity of HuIFN was studied. In this Experiment, fresh blood samples from three volunteers were used after heparinization.

The treated bloods used in this Experiment were as follows: a plasma-free suspension, obtained by centrifuging blood to remove plasma liquid and suspending the residual formed elements in RPMI 1640 medium to give the same element density as that in blood; and an ammonium chloride-treated suspension, obtained by treating blood with Tris-Hcl buffer (pH 7.2) containing 0.75% ammonium chloride in usual way to effect the haemolysis of the erythrocytes, centrifuging the mixture and suspending the resultant erythrocyte-free formed elements in RPMI 1640 medium to give the same element density as that in blood.

One ml aliquots of the heparinized or treated blood were placed in different plastic test tubes which were then added wih 0.1 ml aliquots of physiological saline containing Sendai virus in respective amount of 0, 100, or 1,000 HA, followed by 16-hour incubation at 37° C. The incubated mixtures were uv-irradiated to completely inactivate the Sendai virus, and centrifuged to obtain supernatants which were then assayed for HuIFN titers per ml whole blood.

The HuIFN titer was determined by the dye uptake assay reported in Anne L. R. Pidot, *Applied Microbiology*, Vol. 22, No. 4, pp. 671–677 (1971). The haemagglutination titer (HA) was determined by the method as reported by J. E. Salk, *The Journal of Immunology*, Vol. 49, pp. 87–98 (1944) with slight modification.

The results are given in Table 1.

As is evident from these results, the whole blood and plasma-free suspension containing the whole formed elements of blood are favorable for assaying the HuIFN productivity because of its high and consistent HuIFN productivity. It was also confirmed that the ammonium chloride-treated suspension wherein the erythrocytes were haemolyzed and removed gives a low and inconsistent HuIFN productivity.

TABLE 1

| Treatment | Sendai virus (HA) | Healthy volunteer A | B | C |
| --- | --- | --- | --- | --- |
| No treatment | 0 | 30 | 60 | 10 |
| | 100 | 3,800 | 2,500 | 4,200 |
| | 1,000 | 3,700 | 2,600 | 4,500 |
| Plasma-free suspension | 0 | 0 | 10 | 0 |
| | 100 | 3,600 | 2,400 | 4,600 |
| | 1,000 | 4,100 | 2,800 | 4,200 |
| Ammonium chloride-treated suspension | 0 | 0 | 10 | 0 |
| | 100 | 0 | 200 | 100 |

TABLE 1-continued

| Treatment | Sendai virus (HA) | Healthy volunteer A | B | C |
| --- | --- | --- | --- | --- |
| | 1,000 | 0 | 300 | 70 |

EXPERIMENT 2

Effect of Virus Inoculum on the Productivity of HuIFN

The effect of virus inoculum on the productivity of HuIFN was studied. Fresh blood samples from three healthy volunteers and two cancer patients were used after heparinization.

According to the method as described in Experiment 1, 1 ml aliquots of either heparinized blood sample were placed in different test tubes, added with 0.1 ml aliquots of physiological saline containing Sendai virus in respective amount of 0, 2, 20, 200, 2,000, 20,000, or 200,000 HA, incubated, and assayed for HuIFN titers per ml blood.

A series of experiments using 2,000,000 HA Sendai virus per ml blood was scheduled, but not done because preparation of such a high-titer Sendai virus was unsuccessful.

The results are given in Table 2.

TABLE 2

| Sendai virus (HA) | Healthy volunteer D | E | F | Cancer patient G | H |
| --- | --- | --- | --- | --- | --- |
| 0 | 50 | 80 | 20 | 10 | 0 |
| 2 | 130 | 70 | 30 | 10 | 0 |
| 20 | 2,600 | 1,600 | 5,400 | 10 | 30 |
| 200 | 2,800 | 2,400 | 5,800 | 20 | 70 |
| 2,000 | 4,100 | 2,100 | 6,300 | 20 | 190 |
| 20,000 | 3,500 | 2,300 | 8,800 | 10 | 140 |
| 200,000 | 4,400 | 2,200 | 7,300 | 10 | 180 |
| 2,000,000 | ND | ND | ND | ND | ND |

Note: ND means not done.

As is evident from these results, virus inocula in the range of 20–200,000 HA/ml blood are favorable.

It was confirmed that the blood collected from a cancer patient is much lower in blood HuIFN productivity than those collected from healthy volunteers. This suggests that the assay of blood HuIFN productivity is helpful for the detection of cancer in its early stage.

Several embodiments of the present invention are disclosed hereinafter.

PRODUCTION OF HuIFN

EXAMPLE 1

One ml of a heparinized fresh blood from a healthy volunteer was placed in a plastic test tube, added with 1,000 HA of Sendai virus, incubated at 37° C. for 20 hours, and uv-irradiated to completely inactivate the virus. After centrifuging the mixture, the resultant supernatant was assayed for HuIFN titer.

The HuIFN production was about 3,600 units per ml blood.

EXAMPLE 2

One ml of a heparinized fresh blood from a healthy volunteer was added with 2,000 HA of Newcastle disease virus wherein 90% of the reproductivity has been inactivated. After incubating at 37° C. for 15 hours, the mixture was assayed for HuIFN titer similarly as in Example 1.

The HuIFN production was about 2,800 units per ml blood.

EXAMPLE 3

A heparinized fresh blood from healthy volunteers was centrifuged to remove plasma. The formed elements so obtained were then centrifugally washed in physiological saline, and suspended in RPMI 1640 medium to give the same element density as that in blood.

The resultant suspension was placed in a mini jar, and added wih 500 HA of Sendai virus per ml suspension. After incubating at 37° C. for 16 hours, the mixture was treated and assayed for HuIFN titer similarly as in Example 1.

The HuIFN production was about 3,000 units per ml blood.

EXAMPLE 4

A suspension containing the formed blood elements was prepared similarly as in Example 3.

The suspension was placed in a mini jar, added with 300 units of HuIFN per ml suspension, and incubated at 37° C. for 6 hours. Thereafter, the suspension was further added with 1,000 HA of Sendai virus per ml suspension, and incubated at 37° C. for additional 16 hours. The resultant was treated and assayed for HuIFN similarly as in Example 1.

The HuIFN production was about 27,000 units per ml blood.

ASSAY OF BLOOD HuIFN PRODUCTIVITY

EXAMPLE 5

One ml of a heparinized fresh blood from a healthy volunteer, 28-year old man, was treated similarly as in Example 1, and subjected to bioassay for HuIFN titration.

The HuIFN productivity was about 3,600 units per ml blood.

EXAMPLE 6

One ml of a heparinized fresh blood from a healthy volunteer, 33-year old woman, was treated similarly as in Example 2, and assayed for HuIFN titration similarly as in Example 5.

The HuIFN productivity was about 2,800 units per ml blood.

EXAMPLE 7

A heparinized fresh blood from a healthy volunteer, 61-year old man, was treated similarly as in Example 3 to obtain a suspension containing the formed blood elements.

One ml of the suspension was placed in a plastic test tube, and added with 1,000 HA of Sendai virus. After incubating at 37° C. for 16 hours, the mixture was subjected to double antibody sandwich technique, an enzyme-linked immunosorbent assay, for HuIFN titration.

The HuIFN productivity was about 3,400 units per ml blood. This value was consistent with that obtained by bioassay.

EXAMPLE 8

A heparinized fresh blood from a cancer patient, 68-year old man, was treated similarly as in Example 5 to obtain an HuIFN productivity of about 140 units per ml blood.

EXAMPLE 9

A heparinized fresh blood from a cancer patient, 55-year old woman, was treated similarly as in Example 5 to obtain an HuIFN productivity of about 70 units per ml blood.

It will be obvious to those skilled in the art that various changes and alterations may be made without departing from the scope of the invention and the invention is not to be considered limited to what is described in the specification.

I claim:

1. A clinical assay for detecting human cancer, comprising:
    collecting whole blood from a subject;
    incubating in vitro a predetermined amount of the whole blood in the presence of an anticoagulating effective amount of an anticoagulant and an interferon inducing effective amount of a virus under conditions appropriate for the production of interferon; and
    determining the interferon level in the resultant culture,
    whereby the determination of an interferon level below a predetermined amount is indicative of the possible presence of human cancer.

2. The assay of claim 1, wherein the amount of the virus is in the range of 20–200,000 haemagglutination titers/ml whole blood.

3. The assay of claim 1, wherein said anticoagulant is a member selected from the group consisting of heparin, acid-citrate-dextrose, citrate-phosphate-dextrose, and mixtures thereof.

4. The assay of claim 1, wherein said virus is a member selected from the group consisting of Sendai virus, Newcastle disease virus, and a mixture thereof.

5. The assay of claim 1, wherein the incubation step is carried out at a temperature in the range of 30° to 40° C. for 5 to 50 hours.

6. The assay of claim 1, wherein the determination step is effected by bioassay.

7. The assay of claim 1, wherein the determination step is effected by radioimmunoassay.

8. The assay of claim 1, wherein the determination step is effected by enzyme immunoassay.

9. The assay of claim 1, further including the step of comparing the interferon level obtained in said determining step with a standard to determine whether the interferon level is sufficiently low to warrant a positive indication of the presence of cancer.

10. The assay of claim 1, consisting essentially of said collecting, incubating and determining steps.

11. A clinical assay for detecting human cancer, comprising:
    collecting whole blood from a subject;
    removing the plasma from said whole blood;
    suspending the residual solid in a member selected from the group consisting of saline, isotonic buffer, and nutrient culture medium;
    incubating in vitro a predetermined amount of the resultant cell suspension in the presence of an anticoagulating effective amount of an anaticoagulant and an interferon inducing effective amount of a virus under conditions appropriate for the production of interferon; and determining the interferon level in the resultant culture, whereby the determination of an interferon level below a predetermined amount is indicative of the possible presence of human cancer.

12. The assay of claim 11, wherein the amount of the virus is in the range of 20–200,000 haemagglutination titers/ml whole blood.

13. The assay of claim 11, wherein said anticoagulant is a member selected from the group consisting of heparin, acid-citrate-dextrose, citrate-phosphate-dextrose, and mixtures thereof.

14. The assay of claim 11, wherein said virus is a member selected from the group consisting of Sendai virus, Newcastle disease virus, and a mixture thereof.

15. The assay of claim 11, wherein the incubation step is carried out at a temperature in the range of 30° to 40° C. for 5 to 50 hours.

16. The assay of claim 11, wherein the determination step is effected by bioassay.

17. The assay of claim 11, wherein the determination step is effected by radioimmunoassay.

18. The assay of claim 11, wherein the determination step is effected by enzyme immunoassay.

19. The assay of claim 11, further including the step of comparing the interferon level obtained in said determining step with a standard to determine whether the interferon level is sufficiently low to warrant a positive indication of the presence of cancer.

20. The assay of claim 11, consisting essentially of said collecting, removing, suspending, incubating and determining steps.

* * * * *